United States Patent [19]

König et al.

[11] 4,053,588

[45] Oct. 11, 1977

[54] PHARMACEUTICAL PREPARATIONS HAVING PSYCHOTROPIC ACTIVITY AND PROCESS FOR THEIR MANUFACTURE

[75] Inventors: Wolfgang König, Hofheim, Taunus; Rolf Geiger, Frankfurt am Main; Hans Wissmann, Bad Soden, Taunus; Hansjörg Kruse, Kelkheim, Taunus, all of Germany; Michel Peterfalvi, Paris, France

[73] Assignee: Hoechst Aktiengesellschaft, Frankfurt am Main, Germany

[21] Appl. No.: 576,715

[22] Filed: May 12, 1975

[30] Foreign Application Priority Data

May 14, 1974 Germany .............................. 2423389

[51] Int. Cl.$^2$ ..................... A61K 31/40; A61K 37/00; A61K 37/02

[52] U.S. Cl. ...................................... 424/177; 424/274
[58] Field of Search ............................... 424/274, 177; 260/326.45

[56] References Cited

U.S. PATENT DOCUMENTS

3,002,978   10/1961   Bocher ............................... 260/326.3

FOREIGN PATENT DOCUMENTS

| 63,496 | 9/1968 | Germany | 260/326.45 |
| 4,329,385 | 1943 | Japan | 260/326.45 |

*Primary Examiner*—Stanley J. Friedman
*Attorney, Agent, or Firm*—Curtis, Morris & Safford

[57] ABSTRACT

Pharmaceutical preparations containing an L-pyroglutamic acid amide, processes for their preparation and methods of treating psychotic diseases with them.

1 Claim, No Drawings

PHARMACEUTICAL PREPARATIONS HAVING PSYCHOTROPIC ACTIVITY AND PROCESS FOR THEIR MANUFACTURE

The present invention relates to pharmaceutical preparations having psychotropic activity and to a process for their manufacture.

It is known that the tripeptide amide L-pyroglutamyl-L-histidyl-proline amide (TRH), which is the thyrotropic hormone releasing factor, also has an antidepressive effect. However, in its use as antidepressive agent, this peptide has the drawback of stimulating the secretion of thyrotropic hormone.

It was surprisingly found that simple pyroglutamyl amides show a high antidepressive effect while completely lacking stimulation of thyrotropic hormone secretion.

The present invention provides pharmaceutical preparations having a psychotropic effect which contain or consist of L-pyroglutamyl compounds of formula I

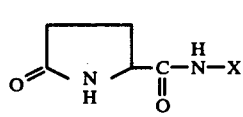

wherein X is an optionally branched alkyl radical having 2 to 6 carbon atoms which may be substituted by a carboxyl group or a carboxamido group.

The substances of formula I can be manufactured according to the usual methods of peptide chemistry. For example an active ester of pyroglutamic acid can be reacted with a corresponding primary amine. Suitable active esters are 4-nitrophenyl ester, 2,4,5-trichlorophenyl ester or pentachlorophenyl ester. Suitable esters for the protection of the carboxyl groups by which the amines can be substituted are the tertiary butyl ester which can be split off by an acid, the benzyl- or 4-nitrobenzyl ester which can be split off by an alkaline agent or by catalytic hydrogenation or the alkyl esters which can be hydrolyzed by an alkaline agent, for example methyl or ethyl esters. The reaction is preferably carried out in a strongly polar solvent, for example dimethyl formamide, dimethyl acetamide or dimethyl sulfoxide, and it can be accelerated by the addition of 1-hydroxybenzotriazole or similar N-hydroxy compounds (cf. French Pat. No. 2,144,416). The pyroglutamyl derivatives still containing carboxyl protecting groups are then converted into the compounds of formula I by splitting off these groups in usual manner.

The pharmaceutical preparations of the invention may contain for example the following active substances: L-pyroglutamic acid ethyl amide, L-pyroglutamic acid propyl amide, L-pyroglutamic acid n-butyl amide, L-pyroglutamic acid isobutyl amide, L-pyroglutamic acid n-pentyl amide, L-pyroglutamic acid n-hexyl amide, L-pyroglutamyl-alanine amide, L-pyroglutamyl-L-leucine amide, L-pyroglutamyl-L-norleucine amide, L-pyroglutamyl-L-valine amide, L-pyroglutamyl-L-isoleucine amide, L-pyroglutamyl-β-alanine, L-pyroglutamyl-β-alanine amide, L-pyroglutamyl-4-amino-butyric acid, L-pyroglutamyl-4-aminobutyric acid amide, L-pyroglutamyl-γ-aminovaleric acid, L-pyroglutamyl-γ-aminovaleric acid amide, L-pyroglutamyl-6-aminohexanoic acid, L-pyroglutamyl-6-aminohexanoic acid amide, L-pyroglutamyl-L-norleucine, L-pyroglutamyl-L-isoleucine and L-pyroglutamyl-L-valine.

In the dopa potentiating test in mice (cf. Everett, Fed. Proc. 23, 198 (1964)), the compounds of formula I show an effect similar to that of the known TRH, however without stimulating the secretion of thyrotropic hormone.

For this reason, the pharmaceutical preparations of the invention may be used for the treatment of psychotic diseases, especially depressive illnesses.

The pharmaceutical preparations of the invention may be in a form suitable for oral administration, for example drops, tablets, dragees or capsules. They may also be in a form suitable for intravenous, intramuscular or subcutaneous administration, for example dissolved in isotonic sodium chloride solution, and they may also be administered via the intranasal route in the form of drops or sprays. The content of active substance is within the range of from 1 to 100% by weight, in solutions from 0.1 to 10 g/100 ml.

Depending on the disease to be treated, the unit dose for oral preparations is generally within the range of form 10 to 1000 mg. For intravenous administration the unit dose is usually from 0.05 to about 5 mg and for intranasal administration from 0.1 to 10 mg. The daily dosage unit for human beings of 75 kg body weight is from one to five times these amounts.

Preparations for parenteral administration advantageously contain, in addition to the active substance, a buffer, for example a phosphate buffer having a pH to held within the range of about 3.5 and 7, moreover, sodium chloride, mannitol or sorbitol to bring the solution to isotonicity. The preparations may be lyophilized or liquid, the latter containing an additive having an antibacterial effect, for example from 0.2 to 0.3% of 4-hydroxybenzoic acid ester.

A preparation for administration via the intranasal route is obtained, for example, by dissolving the active substance in an aqueous buffer solution of 4 to 7.2 and adding a substance to produce isotonicity, for example mannitol, sorbitol or sodium chloride. It is advantageous to add a polymeric adhesive, for example, polyvinyl pyrrolidone and/or a preservative, to the aqueous solution. Such preparations may also contain the pyroglutamyl compounds in the form of an oily suspension or as a fat-containing ointment.

The following Examples illustrate the invention

Manufacture of new pyroglutamyl derivatives of formula I

EXAMPLE 1

L-Pyroglutamic acid n-butyl amide a. L-pyroglutamic acid pentachlorophenyl ester 129 g (1mol) of L-pyroglutamic acid were finely ground in a mortar and suspended in 2 l of tetrahydrofurane. 319 g (1.2 mol) of pentachlorophenol and, at 0° C, 220 g (1.06 mol) of dicyclohexylcarbodiimide dissolved in 300 ml of tetrahydrofurane were added. The mixture was stirred for 1 hour at 0° C and for 5 hours at room temperature. The dicyclohexyl urea was filtered off, and extracted with a small amount of warm tetrahydrofurane. The solvent was distilled off in vacuum. The residue was boiled with isopropanol and filtered off after cooling. After drying under vacuum over $P_2O_5$ and KOH, 175 g product were obtained which melted at 198° C, $[\alpha]_D^{20} 20 = +18.6°$ (c=1, dimethyl formamide)

b. L-pyroglutamic acid n-butyl amide 7.5 g (20 mmols) of L-pyroglutamic acid pentachlorophenyl ester and 1.75 g (2.4 mmols) of n-butyl amine were stirred in 100 ml of tetrahydrofurane for 5 hours. The solvent was distilled off. The residue was dissolved in methanol and treatment with strongly basic and then with strongly acidic ion exchangers followed. After filtration, methanol was distilled off. The oily residue was dissolved and precipitated with petroleum ether. After a prolonged period of time, the product, which has precipitated in oily form, became solid. It was filtered off, washed with petroleum ether and dried under vacuum.

Yield: 2.95 g without sharp melting point.

| $C_9H_{16}N_2O_2$ (184.2) | C | H | N |
|---|---|---|---|
| Calculated: | 58.67 | 8.75 | 15.20 |
| Found: | 58.6 | 8.8 | 14.9 |

EXAMPLE 2

L-Pyroglutamic acid n-hexyl amide 4 ml of n-hexyl amine were added at 0° C to a solution of 3.1 g of L-pyroglutamic acid 2,4,5-trichlorophenyl ester in 10 ml of dimethyl formamide and the solution was left at room temperature for 20 hours. The solvent was removed by distillation in vacuo at room temperature. The residue was taken up in 90% aqueous methanol, and the solution was filtered successively through 200 ml each of Levatit S 100(H+-form) and Serdolit Blau (OH--form). The ion exchanger columns were washed with 200 ml of 90% methanol and the combined eluate and washing solution were concentrated in vacuo. The L-pyroglutamic acid n-hexyl amide obtained as a colorless solid was recrystallized from ethyl acetate.

Yield: 1.33 g, m.p.: 95°
$[E]_D^{20} = +19.8°$ (c=1, dimethyl formamide

EXAMPLE 3

L-Pyroglutamyl-L-alanine amide 3.75 g (10 mmols) of L-pyroglutamic acid pentachlorophenyl ester were stirred in 40 ml of dimethyl formamide with 1.5 g (12 mmols) of L-alanine amide hydrochloride and 1.54 ml (12 mmols) of N-ethylmorpholine for 4 hours. The solvent was distilled off in vacuo. The residue was dissolved in methanol and the solution was stirred successively with strongly basic and strongly acid ion exchangers. The exchanger was removed by filtration and concentration to dryness followed. The residue was triturated with ethyl acetate, dissolved in a little ethanol and precipitated with petroleum ether in the form of a resin that solidified under petroleum ether. Yield: 1.2 g, chromatographically unfirom without sharp melting point.

Calculated: N 21.0; Found: 21.2

EXAMPLE 4

L-Pyroglutamyl-β-alanine 6.75 g (0.05 mol) of 1-hydroxybentriazole and 6.5 g of L-pyroglutamic acid in the form of a fine powder were added to a solution of 9.05 g (0.05 mol) of β-alanine tert. butyl ester hydrochloride and 6.32 ml (0.05 mol) of N-ethyl morpholine in 75 ml of dimethyl formamide. The solution was cooled to −5° C and 11.3 g (0.054 mol) of dicyclohexyl-carbodiimide dissolved in 25 ml of dimethyl formamide were added. The solution was stirred at 0° C for 6 hours and was left for another 16 hours at +4° C. The precipitated dicyclohexyl urea was suction-filtered and the filtrate was concentrated in vacuo at room temperature until it turned to a syrup. The residue was triturated twice with 180 ml of absolute ether, dissolved in 80% methanol and filtered through 200 ml of Serdolit Blau (OH[31] -form). After washing followed with 350 ml of 80% methanol, the combined eluate and washing solutions were evaporated in vacuo at room temperature. The remaining oil was dissolved in 30 ml of 90% trifluoroacetic acid and the solution was stirred for 1 hour at room temperature. The trifluoroacetic acid was evaporated in vacuo and the residue was triturated with absolute ether.

The crude product was recrylatallized from ethanol/ether. Yield: 6.4 g, m.p.: 199° C $[α]_D^{20} = -8.3°$ (c=1, methanol).

EXAMPLE 5

L-Pyroglutamyl-4-aminobutyric acid a. Benzyloxycarbonyl-4-aminobutyric acid tert. butyl ester 600 ml of liquefied isobutylene and 6 ml of conc. $H_2SO_4$ were added to a solution of 172 g of benzyloxycarbonyl-4-aminobutyric acid in 600 ml of methylene chloride. The mixture was shaken for 3 days at room temperature in an autoclave, the isobutylene was distilled off, and the methylene chloride solution was washed twice with 10% sodium carbonate solution and once with water, dried over sodium sulfate and concentrated in vacuo. The residue was dissolved in ether and chromatographed over 620 g of basic $Al_2O_3$. Elution with ether followed.

Yield: 161.9 g (oil)

b. 4-Aminobutyric acid tert. butyl ester hydrochloride

A solution of 161.5 g of benzyloxycarbonyl-4-aminobutyric acid tert. butyl ester in 500 ml of methanol was hydrogenated with palladium catalyst. The pH was maintained at 4.5 by an autotritator and addition of a solution of hydrogen gas in methanol. After the reaction was finished (no further absorption of methanolic HCl), the catalyst was suction-filtered and the filtrate was concentrated. The residue was dissolved in ether and cooled. After some time a precipitate formed, which was suction-filtered.

Yield: 78.2 g, m.p.: 82° - 84° C.

c. L-Pyroglutamyl-4-aminobutyric acid tert. butyl ester 1.3 ml of N-ethylmorpholine and 3.08 g of L-pyroglutamic acid 2,4,5-trichlorophenyl ester were added to a solution of 1.95 g (10 mmols) of 4-aminobutyric acid tert. butyl ester hydrochloride in 20 ml of dimethylformamide. The solution was left overnight at room temperature. It was concentrated, the residue was dissolved in a mixture of ethyle acetate and water, and the ethyl acetate solution was shaken with sodium bicarbonate solution, $KHSO_4$-solution and NaCl-solution, dried with $Na_2SO_4$ and concentrated. The residue was triturated with petroleum ether.

Yield: 2.1 g, m.p.: 68° C.

d. L-Pyroglutamyl-4-aminobutyric acid 2 g of L-pyroglutamyl-4-aminobutyric acid tert. butyl ester were dissolved in 20 ml of trifluoroacetic acid with warming. The solution was left at room temperature for 30 minutes. the trifluoroacetic acid was removed in vacuo and the residue was triturated with ether and suction-filtered. The product was dissolved in water, insoluble material was removed by filtration over active charcoal and the solution was lyophilized.

Yield: 760 mg, m.p.: 117° - 120° $[\alpha]_D^{20} = -11.3°$ (c = 1, methanol).

$C_9H_{14}N_2O_4$(214.2) Calculated: C 50.42; H 6.58; N 13.08;
Found: C 50.6; H 6.5; N 13.2

EXAMPLE 6

L-Pyroglutamyl-4-aminobutyric acid a.
Nα-Benzyloxycarbonyl-Nγ-4,4'dimethoxybenzhydryl-L-glutaminyl-4-aminobutyric acid tert. butyl ester 2.53 g (5 mmols) of Nα-benzyloxycarbonyl-Nγ-4,4'-dimethoxybenzyhydryl-L-glutamine, 975 mg of-aminobutyric acid tert. butyl ester hydrochloride and 675 mg of 1-hydroxybenzotriazole were dissolved in 10 ml of dimethyl formamide. 0.65 ml of N-ethylmorpholine and, at 0° C, a solution of 1.1 g of dicyclohexycarbodiimide in dimethyl formamide were added. The solution was stirred for 1 hour at 0° C and left overnight at room temperature. The precipitate was suction-filtered and the filtrate concentrated. The residue was triturated with sodium bicarbonate solution and water, suction-filtered and dried over $P_2O_5$. The solid was boiled with acetone, cooled to 0° C and suction-filtered. Acetone and petroleum ether were used for washing.

Yield 3.45 g, m.p.: 178° C.

b. L-Pyroglutamyl-4-aminobutyric acid 2.5 g of benzyloxycarbonyl-Nγ-4,4'-dimethoxybenzhydryl-L-glutaminyl-4-aminobutyric acid tert. butyl ester were boiled under reflux for 100 minutes with 2 ml of anisole in 20 ml of trifluoroacetic acid. Concentration followed and the residue was dissolved in a mixture of water and ether. The aqueous phase was clarified with active charcoal and lyophilized. The oily residue was crystallized from methanol/ether.

Yield: 410 mg (about 50%). M.p.: 123° - 124°. Chromatographically identical with the material obtained according to Example 5(d).

EXAMPLE 7

L-Pyroglutamyl-4-aminobutyric acid amide a. Benzyloxycarbonyl-4-aminobutyric acid amide 4.2 ml of triethylene were added to a solution of 7.12 g (30 mmols) of benzyloxycarbonyl-4-aminobutyric acid in 50 ml of tetrahydrofurane. The solution was cooled to −10° C and 2.9 ml of ethyl chloroformate dissolved in 10 ml of absolute tetrahydrofurane were added. The solution was stirred for 10 minutes at −10° C and for 1 hour at room temperature and the precipitate was suction-filtered. The filtrate was concentrated and the residue was dissolved by addition of ethyl acetate and water. The ethyl acetate phase was washed with sodium bicarbonate solution and water, dried and sodium sulfate and concentrated. The residue was triturated with petroleum ether.

Yield: 5.4 g (76%) m.p.: 131° - 132° C.

b. 4-Aminobutyric acid amide hydrochloride.

4 g (16.9 mmols) of benzyloxycarbonyl-4-aminobutyric acid amide were catalytically hydrogenated in methanol in a manner analogous to Example 5(b). the product was crystallized with ether.

Yield: 1.81 g (78%), m.p.: 137° - 138° C.

c. L-Pyroglutamyl-4-aminobutyric acid amide 3.9 g (12.65 mmols) of L-pyroglutamic acid 2,4,5-trichlorophenyl ester were added to a solution of 1.76 g (12.9 mmols) 4-amino butyric acid amide and 1.72 g (12.75 mmols) of 1-hydroxybenzotriazole and 1.65 ml of N-ethylmorpholine in 40 ml of dimethyl formamide. The solution was allowed to stand for 1 hour at room temperature. It was concentrated and triturated with ether. The substance was suction-filtered and chromatographed in methanol/water (1:1) through Serdolit Blau. The eluate was concentrated and the residue was triturated with ether and suction-filtered.

Yield: 1.6 g (58%). For further purification, the product can be recrystallized from ethanol. M.p.: 159° - 160° C, $[\alpha]_D^{20} = -1.9°$ C (c = 1, methanol).

EXAMPLE 8

L-Pyroglutamyl-γ-aminovaleric acid a. L-Pyroglutamyl-γ-aminovaleric acid ethyl ester 1.6 g (0.012 mol) of 1-hydroxybenzotriazole and 7.8 g (0.025 mol) of L-pyroglutamic acid 2,4,5-trichlorophenyl ester were added at 0° C to a solution of 4.25 g (0.025 mol) of γ-aminovaleric acid methyl ester hydrochloride and 3.2 ml of N-ethylmorpholine in 15 ml of dimethyl formamide. The solution was stirred at 0° C for 2 hours and then allowed to stand for 16 hours at +4° C. It was evaporated in vacuo and the crude product was purified by filtration through an acid and a basic ion exchanger resin as has been described in the synthesis of L-pyroglutamyl n-hexyl amide in Example 2. The product was precipitated from ethanol/ether.

Yield: 2.34 g, solification point: 74.5° $[\alpha]_D^{22} = +20.8°$ (c = 1, dimethyl formamide).

b. L-Pyroglutamyl -γ-aminovaleric acid 1.13 g (5 mmols) of L-pyroglutamyl-γ-aminovaleric acid methyl ester were added to a solution of 800 mg (5 mmols) of barium hydroxide octahydrate in 35 ml of water, which solution was stirred for 2.5 hours at room temperature. 2.5 ml (5 mmols) of 2n $H_2SO_4$ were added and the solution was filtered through a clarification layer of kieselguhr to eliminate the precipitated barium sulfate. The peptide was obtained in 80% yield as a colorless amorphous solid by lyophilization of the clear filtrate.

$[\alpha]_D^{22} = +7.3°$ (c = 1, methanol)

Preparations for oral administration

EXAMPLE 9

500 g of pyroglutamic acid n-hexyl amide were mixed with 282 g of potato starch and 560 g of lactose. The mixture was moistened with an alcoholic solution of 8 g of gelatin and granulated. After drying, 60 g of potato starch, 10 g of magnesium stearate, 20 g of highly disperse silicon dioxide and 60 g of talcum were admixed and the mixture was compressed into 10,000 tablets each weighing 150 mg and containing 50 mg of active substance.

EXAMPLE 10

50 g of pyroglutamyl-β-alanine were mixed with 496 g of lactose. The mixture was homogeneously moistened with an aqueous mixture of 4 g of gelatin, and granulated. The dried granules, which were mixed with 20 g of potato starch and 30 g of talcum, were homogeneously filled in 2,000 hard gelatin capsules of size 1. Each capsule contained 25 mg of active substance.

Preparation for intranasal administration

EXAMPLE 11

9 l of distilled water were heated to boiling and 20 g of p-hydroxybenzoic acid methyl ester were dissolved therein. The solution was cooled to about 30° C, 89.58 g of $Na_2HPO_4$, 35.44 g of citric acid, 10 g of sodium chloride and 250 g of mannitol were added and 50 g of pyroglutamyl-4-aminobutyric acid were dissolved therein. The solution was made up with distilled water to a volume of 10 l and filtered.

EXAMPLE 12

31.2 g of $NaH_2PO_4 \cdot 2 H_2O$, 66.29 g of $Na_2HPO_4$, 25 g of sodium chloride and 100 g of benzyl alcohol were dissolved without heating in 8 l of distilled water. 500 g of polyvinyl pyrrolidone having a K-value of 85 to 95 (for example Kollidon (®) 90 of Messrs. BASF) were added and dissolved while stirring. Finally, 200 g of pyroglutamyl-4-aminobutyric acid were added and dissolved while cold. The solution was made up to a volume of 10 l with distilled water and filtered.

EXAMPLE 13 the same procedure was effected as in Example 12. However, polyvinyl alcohol having a K-value of about 90 (for example Mowiol (®) N 90 – 98) was used instead of polyvinyl pyrrolidone.

EXAMPLE 14

50 g of methyl cellulose having an average substitution degree of about 1.5 and a viscosity of 2,700 to 4,000 cP (Tylose(®)MH 4000 p) were suspended in 9 l of distilled water of about 50° C. The suspension was allowed to cool to room temperature, whereupon the methyl cellulose began to swell. A mixture of 400 ml of 1N acetic acid and 282 ml of 1N sodium hydroxide solution was added, then 350 g of mannitol, 500 mg of benzalkonium chloride and 200 g of pyroglutamyl-4-aminobutyric acid amide were dissolved and the solution was made up to a volume of 10 l with distilled water and filtered.

EXAMPLE 15

100 g of microfine pyroglutamyl-β-alanine were made up to a volume of 1 l with liquid paraffin and homogenized.

EXAMPLE 16

10 g of benzyl alcohol were made up to a volume of 0.990 l with 2-octyl dodecanol (for example Eutanol(®)G, Messrs. Henkel and Cie., Dusseldorf). 10 g of microfine pyroglutamyl-4-aminobutyric acid were added and the solution was homogenized.

EXAMPLE 17

40 g of microfine pyroglutamic acid n-hexyl amide and 10 g of benzyl alcohol were made up to a volume of 1 l with a triglyceride mixture of saturated vegetable fatty acids having a medium chain length (for example Miglyol(®), Dynamit Noble, Cologne) and the solution was homogenized.

EXAMPLE 18

20 g of microfine pyroglutamyl-4-aminobutyric acid, 10 g of benzyl alcohol and 40 g of sorbitansesquioleate (for example Arlacel(®)83, Messrs. Atlas Chemie BmbH, Essen) were made up to a volume of 1 l with an oleic acid oleyl ester (for example Cetiol(®), Messrs. Henkel and Cie., Duesseldorf) and the mixture was homogenized.

EXAMPLE 19

10 g of microfine pyroglutamyl-4-aminobutyric acid and 10 g of benzyl alcohol were made up to a volume of 1 l with isopropyl myristate and the mixture was homogenized.

EXAMPLE 20

20 g of a mixture of aluminum-distearates and monostearates (for example Alugel(®) 44 M) were suspended in 0.6 l of a triglyceride mixture of saturated vegetable fatty acids of medium chain length (for example Miglyol (®) 812). The suspension was heated to 150° C and maintained at that temperature for 15 minutes, when it was cooled to room temperature. In a mixture of 0.3 l of the above triglyceride mixture and 10 g of benzyl alcohol, 60 g of microfine pyroglutamyl-β-alanine were suspended. The two suspensions were combined and the final volume was made up to 1 l with the triglyceride mixture of saturated vegetable fat acids of medium chain length.

Preparation for injections

EXAMPLE 21

50 mg of pyroglutamyl-β-alanine were dissolved in 50 ml of bidistilled water to which 10 ml of 1 N phosphate buffer of pH 4.5 was added. The calculated amount of NaCl was added to bring the solution to isotinicity and the volume was made up to 100 ml with water. After sterile filtration the solution was filled into ampoules each containing 1 or 2 ml and lyophilized.

EXAMPLE 22

A solution was prepared according to Example 21, however, before making up the solution to 100 ml with water, 0.25 g of 4-hydroxybenzoic acid methyl ester were added. After sterile filtration. The solution was filled into ampoules each containing 1 or 2 ml.

The preparations for the other compounds of formula I were prepared according to the method described in any one of the Examples 9 – 22.

We claim:

1. A method for treating depression is a patient suffering therefrom, which comprises administering to said patient an effective amount of a compound of the formula

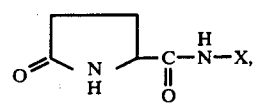

wherein X is branched or unbranched alkyl having 2 to 6 carbon atoms, or branched or unbranched alkyl having 2 to 6 carbon atoms substituted by carboxy or carboxamido.

* * * * *